(12) United States Patent
Ueno et al.

(10) Patent No.: US 7,253,295 B2
(45) Date of Patent: Aug. 7, 2007

(54) CHLORIDE CHANNEL OPENER

(75) Inventors: Ryuji Ueno, Montgomery, MD (US); John Cuppoletti, Cincinnati, OH (US)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 11/333,511

(22) Filed: Jan. 18, 2006

(65) Prior Publication Data

US 2006/0122411 A1 Jun. 8, 2006

Related U.S. Application Data

(62) Division of application No. 10/231,341, filed on Aug. 30, 2002, now Pat. No. 7,064,148.

(60) Provisional application No. 60/372,104, filed on Apr. 15, 2002, provisional application No. 60/315,917, filed on Aug. 31, 2001.

(51) Int. Cl.
*C07C 23/00* (2006.01)
(52) U.S. Cl. .................................................. 554/61
(58) Field of Classification Search ................ 554/61
See application file for complete search history.

(56) References Cited

U.S. PATENT DOCUMENTS

| 5,164,415 A | 11/1992 | Ueno |
| 6,015,828 A | 1/2000 | Cuppoletti |

FOREIGN PATENT DOCUMENTS

| EP | 0310305 A2 | 4/1989 |
| EP | 0430552 A2 | 6/1991 |
| EP | 0690049 A2 | 1/1996 |
| EP | 0978284 A1 | 2/2000 |
| EP | 0979651 A1 | 2/2000 |
| EP | 1082961 A1 | 3/2001 |
| GB | 2075015 A | 11/1981 |
| JP | 2-32055 A | 2/1990 |
| WO | WO 01/70233 A2 | 9/2001 |
| WO | WO 01/76593 A2 | 10/2001 |
| WO | WO 02/089812 A1 | 11/2002 |

OTHER PUBLICATIONS

Database Medline 'Online! Apr. 1, 1998, Deachapunya C et al. "Regulation of chloride secretion across porcine endometrial epithelial cells by prostaglandin E2." Database accession No. NLM9490813 XP002227298.
Hideki Sakai, et al. "A Gastric Housekeeping Cl—Channel Activated via Prostaglandin $EP_3$ Receptor-mediated $Ca^{2+}$/Nitric Oxide/cGMP Pathway", Journal of Biological Chemistry, vol. 270, No. 32, Issue of Aug. 11, 1995, pp. 18781-18785. XP002227295.
Karin A. Yurko-Mauro, et al. "Prostaglandin $F_{2a}$ stimulates CFTR activity by PKA- and PKC-dependent phosphorylation", American Journal of Physiology -Cell Physiology, vol. 275, 1998, pp. C653-C660, XP002227296 abstract.
L.N. Chan, et al. "Activation of an Adenosine 3',5'-Cyclic Monophosphate-Dependent Cl—Conductance in Response to Neurohormonal Stimuli in Mouse Endometrial Epithelial Cells: The Role of Cystic Fibrosis Transmembrane Conductance Regulator[1]", Biology Reproduction, vol. 60, No. 2, 1999, pp. 374-380, XP002227297.
Wilfried Dalemans, et al. "Altered chloride ion channel kinetics associated with the ΔF508 cystic fibrosis mutation", Nature, vol. 354, Dec. 19, 1991, pp. 526-528, XP000611996 ISSN: 0028-0836 abstract.
Esam Z. Dajani, et al. "Effects of E Prostaglandins, Diphenoxylate and Morphine on Intestinal Motility in Vivo", European Journal of Pharmacology, 34 (1975) 105-113, XP001095316 ISSN: 0014-2999.
Sand et al., Journal of Endocrinology, 1995, 147:441-448.
Ueno et al., 1995, CAS:123:75627.

*Primary Examiner*—Joseph K. McKane
*Assistant Examiner*—Rei-tsang Shiao
(74) *Attorney, Agent, or Firm*—Sughrue Mion, PLLC

(57) ABSTRACT

Disclosed is a novel use of a prostaglandin compound as a chloride channel opener. According to the instant invention, chloride channels in a mammalian subject can be opened by a prostaglandin compound to facilitate chloride ion transportation.

5 Claims, No Drawings

CHLORIDE CHANNEL OPENER

CROSS REFERENCE TO RELATED APPLICATIONS

This is a divisional of application Ser. No. 10/231,341 filed Aug. 30, 2002 now U.S. Pat. No. 7,064,148, which claims benefit of Provisional Application No. 60/315,917 filed Aug. 31, 2001, and Provisional Application No. 60/372,104 filed Apr. 15, 2002, the disclosures of which are incorporated herein by reference.

TECHNICAL FIELD

The present invention relates to a method for opening chloride channels. In more detail, the present invention relates to a compound, which can modify transportation of chloride ions.

BACKGROUND ART

It is known that chloride ions (Cl⁻) not only manage transportation of water/electrolyte, secretion and regulation of cell volume but also play an important role as a factor affecting the response of cells.

For example, the transition of chloride ions into or out of cells concurrently accompanies the transport of water and electrolyte, which results in the regulation of cell volume. Therefore, it is suggested that chloride ions play an important role in the growth and division of cells and the programmed cell death that accompany an abrupt change in the cell volume.

In the brain, it is known that inhibitory regulation works in the central nervous system by maintaining chloride ions in the nerve cells at a low level. It is also known that chloride ions play an important role in inhibiting anxiety and spasm, and regulating sleep, memory and circadian rhythm.

In the bowel, it is known that chloride ions are deeply involved with such pathology as diarrhea and constipation, and when opioid such as morphine is administered to bring abnormal secretions of electrolyte such as chloride ions and fluid, it will cause intractable constipation. Other diseases known to be caused by an abnormality in the balance of chloride ions include myotonia atrophica, diseases showing hypercalciuria such as calculus renum, anxiety, insomnia, cystic fibrosis, epilepsia, anesthesia, asthma, bronchitis and neuropathy.

A chloride channel is an ion-transport membrane protein for transporting chloride ions. It has been reported that various kinds of chloride channels are present in the cell membrane of nerve, muscle and epithelium, and they are involved with various physiological functions and cytophylaxis mechanisms.

For example, a chloride channel named CFTR (cystic fibrosis transmembrane conductance regulator) was discovered in trying to find the cause of cystic fibrosis. Cystic fibrosis is an autosomal recessive inheritary disease best known in the Caucasian race. The variation of genes, which is the cause of this disease, occurs in CFTR genes due to the reduced permeability of chloride ions caused by the deficiency in functions of CFTR in the epithelial cells of air duct, pancreas, bowel, perspiratory gland, alimentary tract, etc.

Further, a chloride channel cloned by cramp fish's electric organ and named ClC-0 was later found to form a large family (ClC family). Examples of ClC family are: ClC-1 present in the skeletal muscle of mammals; ClC-2 present in the epithelium of various organs; ClC-3 and ClC-4 distributed in hippocampus, cerebellum, etc.; ClC-5 present in lung, kidney, etc.; ClC-6 and ClC-7 present in brain, testis, skeletal muscle, kidney, etc.; and ClCK-1 and ClCK-2 specifically shown only in kidney. It is known that the abnormality in ClC-1 causes congenital myotonia and the abnormality in ClC-5 causes hereditary nephrolithiasis.

Accordingly, a compound which can open chloride channels and promotes chloride ion transportation are considered to affect on various cell functions and cytophylaxis mechanisms, and also considered to be useful for the treatment of pathology occurring because of abnormal chloride ion balance within or outside the cells due to the reduced permeability of chloride ions by some cause.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

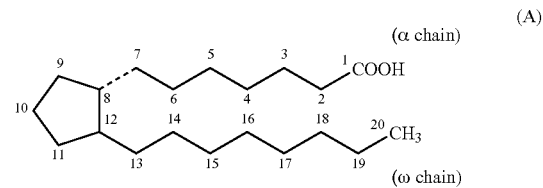

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15—OH
Subscript 2: 5,6- and 13,14-diunsaturated-15—OH
Subscript 3: 5,6-, 13,14-, and 17,18-triunsaturated-15—OH.

Further, the PGFs are classified, according to the configuration of the hydroxyl group at the 9-position, into α type (the hydroxyl group is of an α-configuration) and β type (the hydroxyl group is of a β-configuration).

$PGE_1$, $PGE_2$ and $PGE_3$ are known to have vasodilation, hypotension, gastric secretion decreasing, intestinal tract movement enhancement, uterine contraction, diuretic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

It has been reported that $PGE_1$ and $PGF_{2\alpha}$ stimulate secretion of chloride ions in rabbit ileum (Nature vol. 238, 26-27, 1972, the cited reference is herein incorporated by reference) and $PGE_2$ induces secretion of chloride ions in human jejunum (Gastroenterology vol. 78, 32-42, 1980, the cited reference is herein incorporated by reference). It has been also reported that $PGE_2$ regulates chloride ion transportation in the endometrial epithelial cells (Journal of Physiology vol. 508, 31-47, 1998, the cited reference is herein incorporated by reference). Meanwhile, it has been reported that platelet chloride transportation did not respond to $PGE_1$ in cystic fibrosis patients (European Journal of Clinical Chemistry and Clinical Biochemistry vol. 33, No. 6, 329-335, 1995, the cited reference is herein incorporated by reference) and a prostaglandin analogue (misoprostol) did not promote chloride secretion in cystic fibrosis patients (American Journal of Human Genetics Vol. 67, No. 6, 1422-1427, 2000, the cited reference is herein incorporated by reference).

Further, it has been reported that $PGE_2$ opens a housekeeping basolateral chloride channel of rabbit (Journal of Biological Chemistry, 270(32) 1995, the cited reference is herein incorporated by reference). Furthermore, it has been reported that $PGE_2$ and $PGF_{2\alpha}$ activate chloride conductance in mouse endometrial epithelial cells via CFTR (Biology of Reproduction, 60(2) 1999).

However, it is not known how prostaglandin compounds act on chloride channels, especially on ClC channels.

DISCLOSURE OF THE INVENTION

The present inventors have conducted intensive studies and found that a prostaglandin compound opens chloride channels, especially ClC channels, which resulted in the completion of the present invention.

Namely, the present invention relates to a method for opening ClC channels in a mammalian subject, which comprises administration of an effective amount of a prostaglandin compound to the subject. Particularly, the present invention relates to a method for treating conditions associated with reduced chloride ion permeability, which comprises opening ClC channels by administrating an effective amount of a prostaglandin compound to a subject in need of such treatment.

The present invention further relates to a pharmaceutical composition for opening ClC channels, which comprises an effective amount of a prostaglandin compound. Particularly, the present invention relates to a pharmaceutical composition for treating a condition associated with reduced chloride ion permeability in a mammalian subject, which comprises an effective amount of a prostaglandin compound.

Further more, the present invention relates to use of a prostaglandin compound for manufacturing a pharmaceutical composition for opening ClC channels in a mammalian subject. Particularly, the present invention relates to use of a prostaglandin compound for manufacturing a pharmaceutical composition for treating a condition associated with reduced chloride ion permeability.

DETAILED DESCRIPTION OF THE INVENTION

The nomenclature of the PG compounds used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the α-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substuents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A preferred compounds used in the present invention is represented by the formula (I):

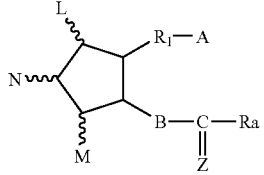

wherein L, M and N are hydrogen, hydroxy, halogen, lower alkyl, hydroxy(lower)alkyl, or oxo, wherein at least one of L and M is a group other than hydrogen, and the five-membered ring may have at least one double bond;

A is —CH$_2$OH, —COCH$_2$OH, —COOH or a functional derivative thereof;

B is —CH$_2$—CH$_2$—, —CH═CH— or —C≡C—;

Z is

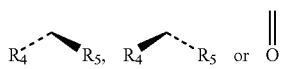

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; cyclo(lower)alkyl; cyclo(lower)alkyloxy; aryl; aryloxy; heterocyclic group; heterocyclic-oxy group.

A preferred compounds used in the present invention is represented by the formula (II):

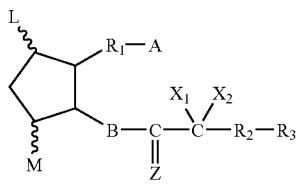

wherein L and M are hydrogen, hydroxy, halogen, lower alkyl, hydroxy(lower)alkyl, or oxo, wherein at least one of L and M is a group other than hydrogen, and the five-membered ring may have one or more double bonds;

A is —CH$_2$OH, —COCH$_2$OH, —COOH or a functional derivative thereof;

B is —CH$_2$—CH$_2$—, —CH═CH— or —C≡C—;

Z is

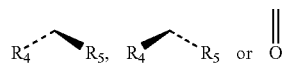

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, cyclo(lower)alkyl, cyclo(lower)alkyloxy, aryl, aryloxy, heterocyclic group or heterocyclic-oxy group.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino) ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred examples of L and M include hydroxy and oxo, and especially, M is hydroxy and L is oxo which has a 5-membered ring structure of, so called, PGE type.

Preferred example of A is —COOH, its pharmaceutically acceptable salt, ester or amide thereof.

Preferred example of $X_1$ and $X_2$ is fluorine, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur.

Examples of $R_1$ include, for example, the following groups:

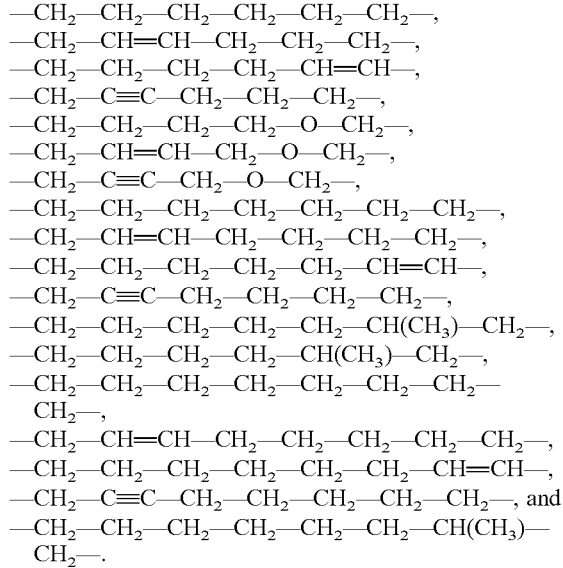

Preferred Ra is a hydrocarbon containing 1-10 carbon atoms, more preferably, 1-8 carbon atoms. Ra may have one or two side chains having one carbon atom.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the PG compound which is dihydro between 13 and 14, and keto(=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivatives thereof.

The bicyclic compound is represented by the formula (III)

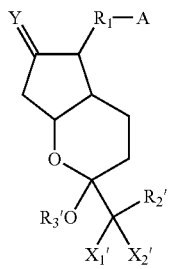

(III)

whererin, A is —$CH_2OH$, —$COCH_2OH$, —COOH or a functional derivative thereof;

$X_1'$ and $X_2'$ are hydrogen, lower alkyl, or halogen;

Y is

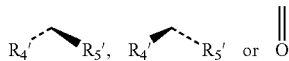

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group; and $R_2'$ is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; cyclo(lower)alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 these cited references are herein incorporated by reference).

Further more, the instant inventor has found a novel compound represented by the formula (IV):

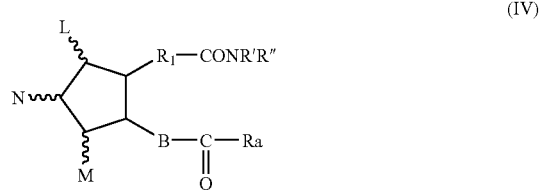

(IV)

wherein L, M, N, B, $R_1$ and Ra are the same as those defined in the formula (I); and R' and R" are hydrogen, lower alkyl, aryl, alkyl- or aryl-sulfonyl, lower alkenyl or lower alkynyl is also effective for opening chloride channels. Accordingly, the present invention also covers the novel compound as above.

According to the present invention a mammalian subject may be treated by the instant invention by administering the compound used in the present invention. The subject may be any mammalian subject including a human. The compound may be applied systemically or topically. Usually, the compound may be administered by oral administration, intravenous injection (including infusion), subcutaneous injection, intra rectal administration, intra vaginal administration, transdermal administration, ophthalmic administration and the like. The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.0001-100 mg/kg per day.

The compound may preferably be formulated in a pharmaceutical composition suitable for administration in a conventional manner. The composition may be those suitable for oral administration, injection or perfusion as well as it may be an external agent, ophthalmic agent, suppository or pessary.

The composition of the present invention may further contain physiologically acceptable additives. Said additives may include the ingredients used with the 15-keto-PG compound such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.00001-10.0 wt %, more preferably 0.0001-1.0 wt %.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary. They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

The composition may be an ophthalmic composition such as eye drops or eye ointment. The eye drops may be prepared by dissolving active ingredients in a sterile aqueous solution such as physiological saline and buffering solution, or by combining powder components to provide a powdery composition to be dissolved before use. The eye ointment may be prepared by mixing active ingredients into a conventional ointment base.

The present external agent includes all the external preparations used in the fields of dermatology and otolaryngology, which includes ointment, cream, lotion and spray.

Another form of the present invention is suppository or pessary, which may be prepared by mixing active ingredients into a conventional base such as cacao butter that softens at body temperature, and nonionic surfactants having suitable softening temperatures may be used to improve absorbability.

The term "treatment" used herein includes any means of control such as prevention, care, relief of the condition, attenuation of the condition and arrest of progression.

The above-described compounds open chloride channels, especially ClC channels, which enable to regulate various cell functions and cytophylaxis mechanisms. Especially, the present compounds may be applied for the treatment of condition associated with reduced permeability of chloride ions.

The term "open ClC channel" used herein includes activating, promoting or modulating the Cl$^-$ current, Cl$^-$ secretion or Cl$^-$ transport by opening the ClC channel.

Examples of the condition associated with reduced permeability of chloride include, but are not limited to, myotonia atrophia, diseases showing hypercalciuria such as calculus renum, constipation, anxiety, insomnia, cystic fibrosis, epilepsia, anesthesia, asthma, bronchitis and neuropathy.

Since the present compounds open especially ClC-2 channels, they are useful for the treatment of diseases such as cystic fibrosis, congenital myotonia and hereditary nephrolithiasis, which are caused by the reduced functions of chloride channels other than ClC-2 channels.

The pharmaceutical composition of the present invention may further contain other pharmacological ingredients as far as they do not contradict the purpose of the present invention.

The further details of the present invention will follow with reference to test examples, which, however, are not intended to limit the present invention.

SYNTHESIS EXAMPLE 1

Preparation of 13,14-dihydro-15-keto-17-phenyl-18,19,20-trinor-PGF$_{2\alpha}$ N-ethylamide (5)

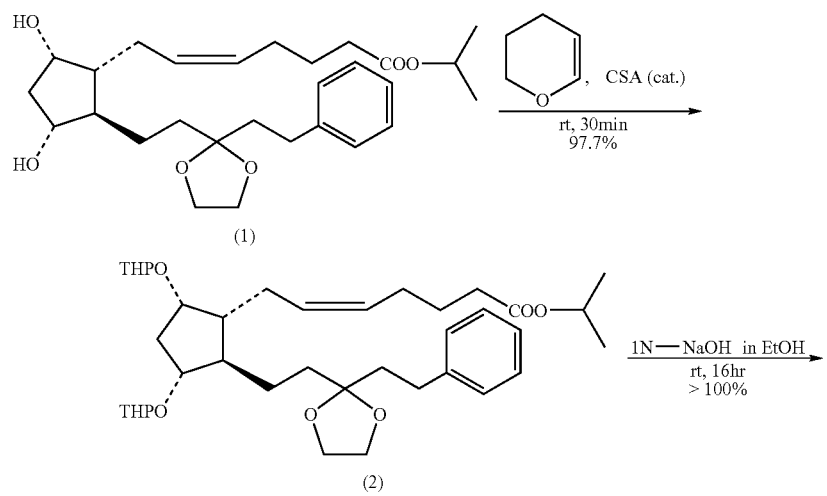

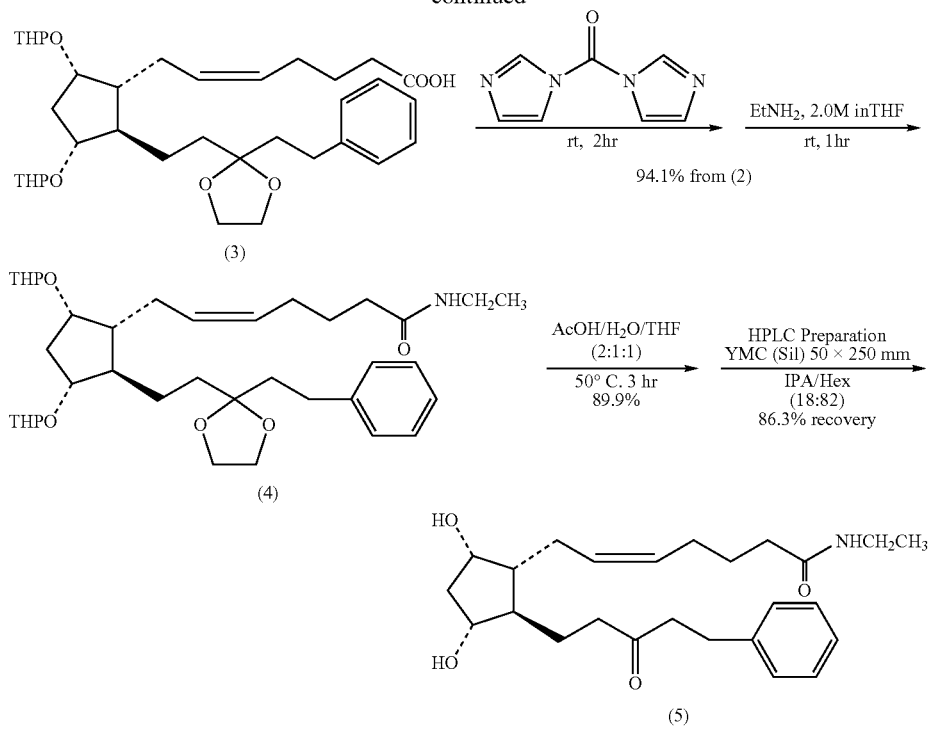

(1)→(2)

3,4-dihydro-2H-pyran (0.70 ml, 7.67 mmol) was added to the solution of Compound (1)(0.350 g, 0.737 mmol) in anhydrous dichloromethane (10 ml). To the solution, camphor sulfonic acid (7 mg, 0.03 mmol) was added. The mixture was stirred for 30 min at room temperature. The reaction mixture was poured into saturated aqueous sodium bicarbonate and extracted with dichloromethane twice. The organic layer was dried over anhydrous magnesium sulfate and evaporated. Chromatography on a Silica gel column (BW-300 150 g, ethyl acetate:hexane=1:3) of the residue on evaporation gave Compound (2)(0.463 g, 0.720 mmol, 97.7% yield) as a colorless oil.

(2)→(3)

To the solution of Compound (2) (0.889 g, 1.38 mmol) in ethanol (14 ml), 1N-sodium hydroxide aqueous solution(6.9 ml, 6.9 mmol) was added. The reaction mixture was stirred for 16 hrs at room temperature. The mixture was cooled in ice-bath, and then ethyl acetate and water were added to the mixture.1N-hydrochloric acid (7 ml, 7 mmol) was added until the pH of the mixture became 4. The mixture was extracted with ethyl acetate for 3 times. The combined organic layer was washed with saturated aqueous sodium chloride twice and then dried over anhydrous magnesium sulfate. Evaporation of the organic layer gave crude Compound (3)(0.878 g) as a colorless oil. The crude Compound (3) was used for the following reaction without purification.

(3)→(4)

Carbonyldiimidazole (0.448 g, 2.77 mmol) was added to the solution of crude Compound (3)(0.878 g, 1.38 mmol) in anhydrous THF (9.0 ml). The mixture was stirred for 2 hrs at room temperature. 2M-Ethylamine in THF solution (2.77 ml, 5.54 mmol) was added to the reaction mixture. The mixture was stirred for 1 hr at room temperature and poured into 1N-hydrochloric acid, and then extracted with ethyl acetate for 3 times. The combined organic layer was washed with saturated aqueous sodium bicarbonate and saturated aqueous sodium chloride. The organic layer was dried over anhydrous magnesium sulfate and evaporated. Chromatography on a Silica gel column (FL-60D 150 g, ethyl acetate: hexane=3:1) of the residue gave Compound (4) (0.817 g, 1.30 mmol, 94.1% yield based on Compound (2)).

(4)→(5)

Acetic acid (9.8 ml) and water (4.9 ml) were added to the solution of Compound (4) (0.815 g, 1.30 mmol) in THF (4.9 ml). The mixture was stirred for 3 hrs at 50° C. and then cooled to 0° C. 2N-sodium hydroxide aqueous solution was added to the mixture until the pH of the mixture became 9. The mixture was extracted with ethyl acetate for 3 times. The combined organic layer was washed with water and saturated aqueous sodium chloride. The organic layer was dried over anhydrous magnesium sulfate and evaporated. Chromatography on a Silica gel column (FL-60D 100 g, 2-propanol:ethyl acetate=5:100) of the residue gave colorless oil (0.485 g, 1.17 mmol, 89.9% yield). Further purification with preparative HPLC (YMC-Pak RI-053-15, φ50*250 mm-SIL 120 A, 2-propanol:n-hexane=18:82, solvent flow=100 ml/min) gave Compound (5) (0.417 g, 1.12 mmol, 86.3% yield).

hu 1H-NNR spectrum (200 MHz/CDCl$_3$) of Compound (5)

δ (TMS=0 ppm)

7.33-7.13 (5H, m), 5.84(1H, br), 5.28-5.50 (2H, m), 4.18-4.07 (1H, m), 3.90-3.80 (1H, m), 3.26 (2H, dq, J=5.6, 7.3 Hz), 3.20 (2H, br), 2.94-2.86 (2H, m), 2.80-2.71 (2H, m), 2.60-2.52 (2H, m), 2.50-1.90 (4H, m), 2.17 (2H, t, J=7.0 Hz) 1.90-1.56 (6H, m), 1.47-1.25 (2H, m), 1.13 (3H, t, J=7.3 Hz)

SYNTHESIS EXAMPLE 2

Preparation of N1-ethyl-7-[(2,4aR,5R,7aR)-2-(1,1-difluoropentyl)-2-hydroxy-6-oxoperhydrocyclopenta[b]pyran-5-yl]heptanamide (7)

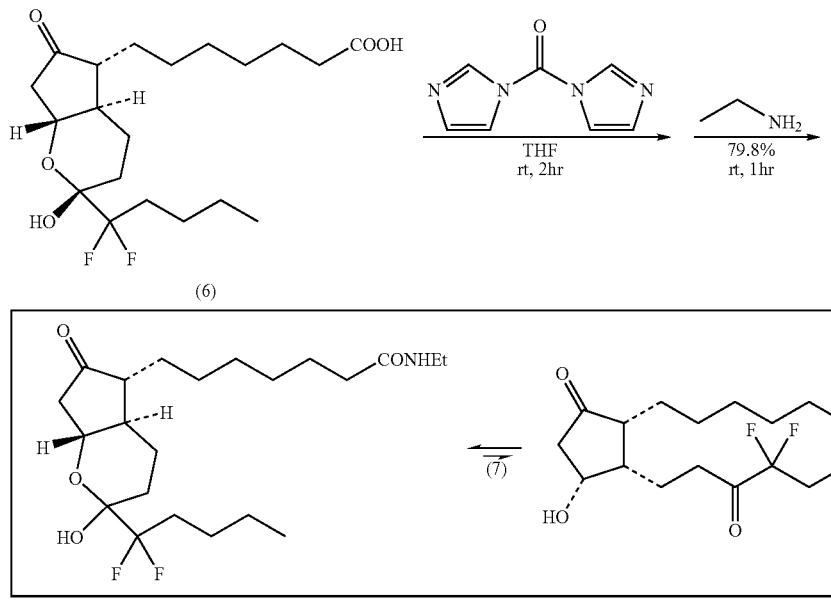

Sub Lot-1

Carbonyldiimidazole (79.5 mg, 0.490 mmol) was added to the solution of Compound (6) (174.0 mg, 0.446 mmol) in anhydrous THF (5 ml). The mixture was stirred for 3 hrs at room temperature and then 2M-ethylamine in THF solution (0.87 ml, 1.74 mmol) was added to the mixture. The mixture was stirred for 12 hrs at room temperature. Saturated aqueous ammonium chloride (10 ml) and ethyl acetate (10 ml) were added to the reaction mixture with stirring. The aqueous layer was separated from the organic layer and extracted with ethyl acetate for 3 times. The combined organic layer was dried over magnesium sulfate and then evaporated. Chromatography on a Silica gel column (FL-60D 10 g, hexane:ethyl acetate=1:2) of the residue gave colorless oil (117.5 mg, 0.281 mmol, 63.0% yield).

Sub-Lot 2

Carbonyldiimidazole (105.9 mg, 0.653 mmol) was added to the solution of Compound (6) (229.2 mg, 0.587 mmol) in anhydrous THF (3 ml). The mixture was stirred for 2 hrs at room temperature and then 2M-ethylamine in THF solution (1.2 ml, 2.4 mmol) was added to the mixture. The mixture was stirred for 1 hr at room temperature. Saturated aqueous ammonium chloride (10 ml) and ethyl acetate (10 ml) were added to the reaction mixture with stirring. The aqueous layer was separated from the organic layer and extracted with ethyl acetate twice. The combined organic layer was dried over magnesium sulfate and then evaporated. Chromatography on a Silica gel column (FL-60D 10 g, hexane:ethyl acetate=2:3) of the residue gave colorless oil (195.7 mg, 0.469 mmol, 79.8% yield).

These 2 sub lots described above were consolidated. Further purification of the consolidated product (301.4 mg) with preparative HPLC (Merck Lichrosorb DIOL-7 µm, ϕ25*250 mm, 2-propanol:n-hexane=10:100, solvent flow=40 ml/min) gave Compound (7) (209.6 mg, 69.5% recovery).

$^1$H-NNR Spectrum (200 MHz/CDCl$_3$) of Compound (7) δ (TMS=0 ppm)

5.42 (1H, br), 4.26-4.10 (1H, m), 3.29 (2H, dq, J=5.6, 7.2 Hz), 2.83 (1H, br), 2.58 (1H, dd, J=17.6, 7.3 Hz), 2.21 (1H, dd, J=17.6, 11.5 Hz), 2.14 (2H, t, J=7.5 Hz), 2.10-1.73 (5H, m), 1.73-1.21 (17H, m), 1.14 (3H, t, J=7.2 Hz), 0.94 (3H, t, J=7.1 Hz)

SYNTHESIS EXAMPLE 3

Preparation of N1-ethyl-7-[(2,4aR,5R,6S,7aR)-2-(1,1-difluoropentyl)-2,6-dihydroxyperhydrocyclopenta[b]pyran-5-yl]heptanamide(15)

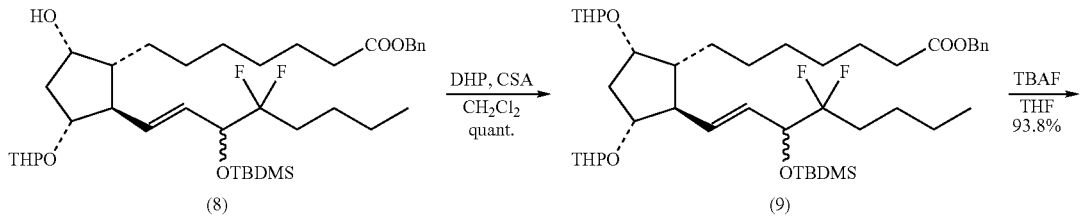

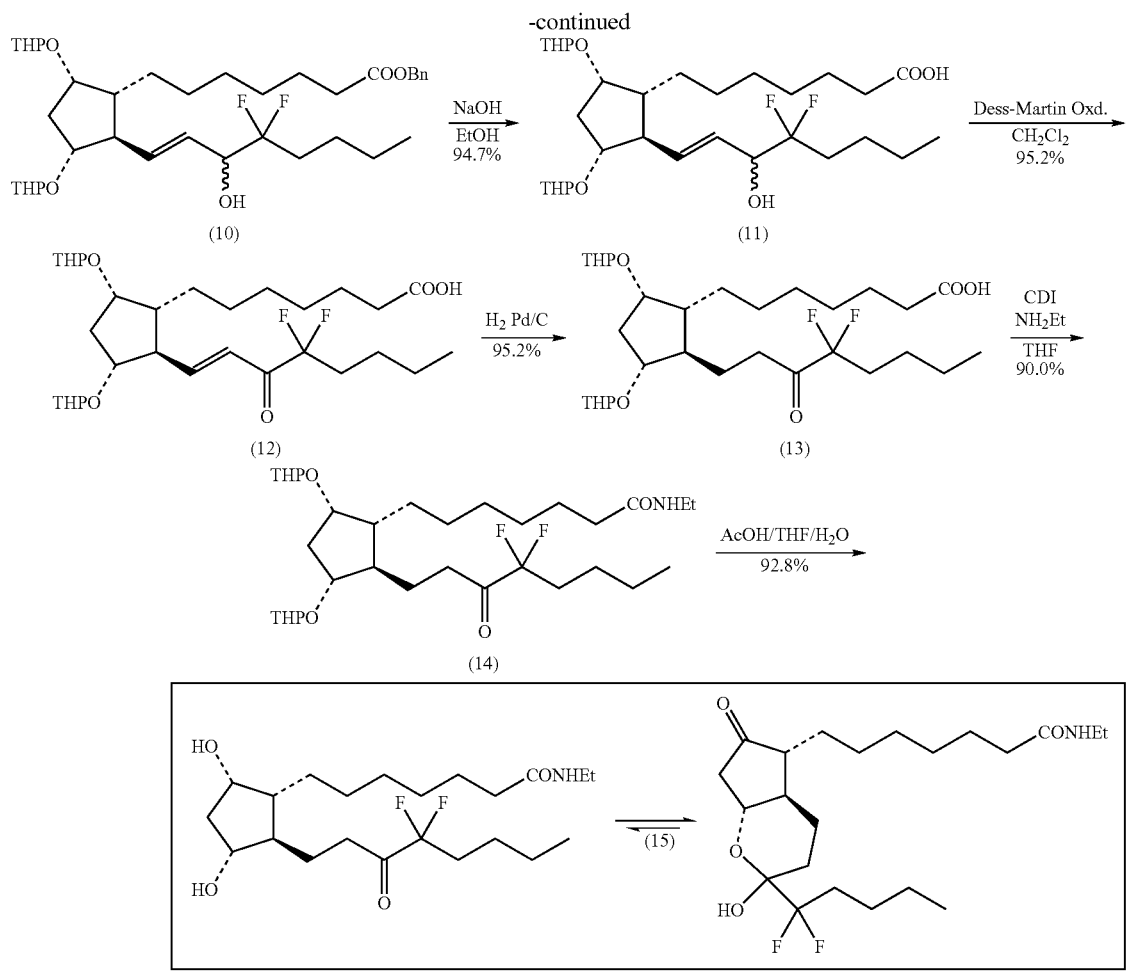

(8)→(9)

3,4-dihydro-2H-pyran (4.22 ml, 46.11 mmol) and camphor sulfonic acid (42.16 mg, 0.181 mmol) were added to the solution of Compound (8) (2.87 g, 4.216 mmol) in anhydrous dichloromethane (90 ml) at 0° C. The reaction mixture was stirred for 50 min at 0° C. Saturated aqueous sodium bicarbonate was added to the reaction mixture. The mixture was warmed to room temperature and then extracted with dichloromethane (50 ml) for 3 times. The combined organic layer was washed with water (180 ml) and saturated aqueous sodium chloride (180 ml). The organic layer was dried over anhydrous magnesium sulfate and then evaporated. Chromatography on a Silica gel column (BW-300 154 g, hexane:ethyl acetate=8:1) of the residue gave Compound (9) (3.42 g, 4.476 mmol, quantitative yield).

(9)→(10)

1M-tetrabutylammonium fluoride in THF solution (5.371 ml, 5.371 mmol) was dropped to the solution of Compound (9) (3.42 g, 4.476 mmol) in anhydrous THF (10.7 ml) at 0° C. The mixture was stirred for 4 hrs at room temperature. Aqueous ammonium acetate (200 mg/ml, 10.3 ml) was added to the reaction mixture. The mixture was stirred for 10 min and then extracted with diisopropyl ether for 3 times. The combined organic layer was washed with aqueous sodium bicarbonate and saturated aqueous sodium chloride (50 ml). The organic layer was dried over anhydrous magnesium sulfate and then evaporated. Chromatography on a Silica gel column (BW-300 170 g, hexane:ethyl acetate=3:1) of the residue gave Compound (10) (2.73 g, 4.200 mmol, 93.8% yield).

(10)→(11)

The solution of Compound (10) (130.4 mg, 0.200 mmol) in ethanol (2 ml) was cooled to 0° C. 1N-sodium hydroxide aqueous solution (0.8 ml, 0.80 mmol) was dropped to the solution below 15° C. The mixture was stirred for 3.6 hrs at room temperature and then evaporated. To the residue, water (1 ml) was added and the pH of the mixture was regulated to 3-4 by the addition of diluted hydrochloric acid. The mixture was extracted with ethyl acetate (20 ml) for 3 times. The combined organic layer was washed with water (30 ml, twice) and saturated aqueous sodium chloride (30 ml). The organic layer was dried over anhydrous magnesium sulfate and then evaporated. Chromatography on a Silica gel column (15%-water containing FL-60D 10 g, hexane:ethyl acetate=3:2) of the residue gave Compound (11) (106.2 mg, 0.1894 mmol, 94.7% yield).

(11)→(12)

Dess-Martin periodinane (1.68 g, 3.970 mmol) was added to the solution of Compound (11) (1.21 g, 1.985 mmol) in anhydrous dichloromethane (63 ml) at 0° C. The reaction mixture was stirred for 1 hr at room temperature. Aqueous sodium thiosulfate (39.8 ml) was added to the reaction mixture. Then the reaction mixture was extracted with ethyl acetate (50 ml) for 3 times. The combined organic layer was washed with saturated aqueous sodium bicarbonate and saturated aqueous sodium chloride. The organic layer was dried over anhydrous magnesium sulfate and then evaporated. Chromatography on a Silica gel column (15%-water containing FL-60D 55 g, hexane:ethyl acetate=3:1) of the residue gave Compound (12) (1.06 g, 1.890 mmol, 95.2% yield).

(12)→(13)

10%-paradium on charcoal (69.1 mg) was added to the solution of Compound (12) (345.7 mg, 0.619 mmol) in ethyl acetate (34.6 ml). The mixture was stirred for 3 hrs in hydrogen atmosphere. The reaction mixture was filtrated through a Celite® pad to remove the catalyst. The consecutive operations described above were repeated for 5 times to complete the hydrogenation reaction. Concentration of the filtrate gave Compound (13) (330.4 mg, 0.589 mmol, 95.2% yield).

(13)→(14)

Carbonyldiimidazole (143.4 mg, 0.884 mmol) was added to the solution of Compound (13) (330.4 mg, 0.589 mmol) in anhydrous THF (6.7 ml). The mixture was stirred for 3 hrs at room temperature. To the reaction mixture, 2M-ethylamine in THF solution (0.589 ml, 1.179 mmol) was added and stirred for 1 hr at room temperature. To the reaction mixture, saturated aqueous ammonium chloride was added. The mixture was extracted with ethyl acetate (20 ml) for 3 times. The combined organic layer was washed with saturated aqueous sodium bicarbonate (50 ml) and saturated aqueous sodium chloride (50 ml). The organic layer was dried over anhydrous magnesium sulfate and then evaporated. Chromatography on a Silica gel column (15%-water containing FL-60D 16.5 g, hexane:ethyl acetate=2:1) of the residue gave Compound (14) (311.6 mg, 0.530 mmol, 90.0% yield).

(14)→(15)

Acetic acid (4.2 ml) and water (2.1 ml) were added to the solution of Compound (14) (344.0 mg, 0.585 mmol) in THF (2.1 ml). The mixture was stirred for 3 hrs at 50° C. and then cooled to 0° C. 2N-sodium hydroxide aqueous solution was added to the reaction mixture. The mixture was extracted with ethyl acetate (50 ml) for 3 times. The combined organic layer was washed with water (35 ml) and saturated aqueous sodium chloride (35 ml) twice. The organic layer was dried over anhydrous magnesium sulfate and then evaporated. Chromatography on a Silica gel column (15%-water containing FL-60D 14 g, hexane:ethyl acetate=1:1 and then changed to ethyl acetate) of the residue gave Compound (15) (227.9 mg, 0.543 mmol, 92.8% yield). Further purification with preparative HPLC (Merck Lichrosorb DIOL-7 μm, 25*250 mm, 2-propanol:n-hexane=12:88, solvent flow=35 ml/min) gave Compound (15) (151.0 mg, 0.3599 mmol, 61.5% yield).

$^1$H-NNR Spectrum (200 MHz/CDCl$_3$) of Compound (15) δ 5.43 (1H, br), 4.32-4.15 (1H, m), 3.96-3.84 (0.28H, m), 3.79-3.61 (0.72H, m), 3.29 (2H, dq, J=5.6, 7.3 Hz), 2.86-2.80 (0.55H, m), 2.70-2.64 (0.55H, m), 2.54 (0.72H, dd, J=15.8, 7.0 Hz), 2.43 (0.72H, dd, J=15.8, 5.2 Hz), 2.15 (2H, t, J=7.1 Hz), 2.25-1.09 (23.45H, m), 1.14 (3H, t, J=7.2 Hz), 0.92 (3H, t, J=7.1 Hz)

SYNTHESIS EXAMPLE 4

Preparation of 13,14-dihydro-15-keto-20-ethyl-PGF$_{2\alpha}$N-ethylamide (20)

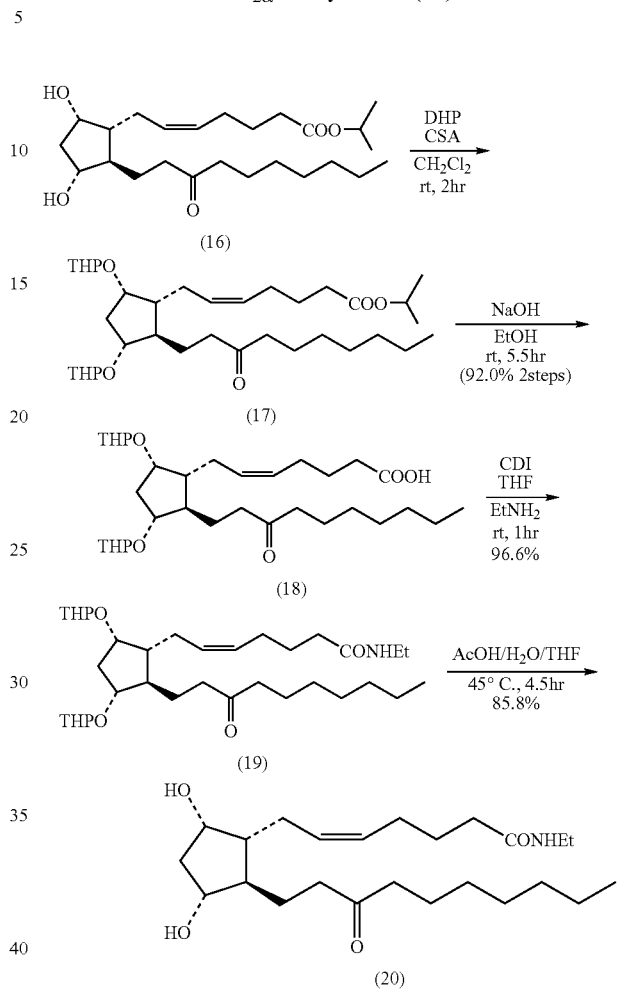

(16)→(17)

3,4-dihydro-2H-pyran (2 ml, 21.9 mmol) and camphor sulfonic acid (20 mg, 0.09 mmol) were added to the solution of Compound (16) (1.00 g, 2.36 mmol) in anhydrous dichloromethane (30 ml). The mixture was stirred for 2 hrs. To the reaction mixture, saturated aqueous sodium bicarbonate (20 ml) was added and stirred vigorously. The aqueous layer was separated from the organic layer and extracted with dichloromethane twice. The combined organic layer was washed with water and saturated aqueous sodium chloride. The organic layer was dried over anhydrous magnesium sulfate and then evaporated. Chromatography on a Silica gel column (BW-300 70 g, hexane:ethyl acetate=3:7) of the residue gave Compound (17) (1.45 g, 2.45 mmol, quantitative yield).

(17)→(18)

1N-sodium hydroxide aqueous solution (11.8 ml, 11.8 mmol) was added to the solution of Compound (17) (1.45 g, 2.36 mmol) in ethanol (20 ml) at 0° C. The mixture was warmed to room temperature and stirred to 5.5 hrs. The mixture was acidified at 0° C. with 1N-Hydrochloric acid (12.4 ml, 12.4 mmol). The mixture was extracted with ethyl acetate for 3 times. The combined organic layer was washed with water and saturated aqueous sodium chloride. The organic layer was dried over anhydrous magnesium sulfate and then evaporated. Chromatography on a Silica gel column (15%-water containing FL-60D 14 g, hexane:ethyl acetate=10:0→9:1→8:2→7:3→6:4→5:5→4:6→3:7) of the residue gave Compound (18) (1.19 g, 2.16 mmol, 92.0% yield)

(18)→(19)

Carbonyldiimidazole (265 mg, 1.64 mmol) was added to the solution of Compound (18) (600.3 mg, 1.09 mmol) in anhydrous THF (10 ml). The mixture was stirred for 1.5 hrs at room temperature. To the mixture, 2M-ethylamine THF solution (3.0 ml, 6.0 mmol) was added and stirred for 1 hr. The reaction mixture was cooled to 0° C. and acidified (pH=3) by the addition of cold 1N-hydrochloric acid. The mixture was extracted with ethyl acetate for 3 times. The combined organic layer was washed with saturated aqueous sodium bicarbonate and saturated aqueous sodium chloride. The organic layer was dried over anhydrous magnesium sulfate and then evaporated. Chromatography on a Silica gel column (FL-60D 25 g, hexane:ethyl acetate=1:1) of the residue gave Compound (19) (497.0 mg, 0.86 mmol, 78.9% yield). Simultaneously, Compound (18) (117.4 mg, 19.6% recovery) was recovered.

Carbonyldiimidazole (69.0 mg, 0.43 mmol) was added to the solution of recovered Compound (18) (117.4 mg) in anhydrous THF (2 ml). The mixture was stirred for 2 hrs at room temperature. To the mixture, 2M-ethylamine THF solution (3.0 ml, 6.0 mmol) was added and stirred for 1 hr. The reaction mixture was cooled to 0° C. and then acidified (pH=3) by the addition of cold 1N-hydrochloric acid. The mixture was extracted with ethyl acetate for 3 times. The combined organic layer was washed with saturated aqueous sodium bicarbonate and saturated aqueous sodium chloride. The organic layer was dried over anhydrous magnesium sulfate and then evaporated. Chromatography on a Silica gel column (FL-60D 5 g, hexane:ethyl acetate=1:1) of the residue gave Compound (19) (113.2 mg, 0.20 mmol, 92.0% yield). The 2 batches described above were consolidated and 610 mg of Compound (19) was obtained.

(19)→(20)

Acetic acid (6 ml) and water (2 ml) were added to the solution of Compound (19) (603.0 mg, 1.07 mmol) in THF (2 ml). The mixture was stirred for 2.5 hrs at 45° C. and then cooled to room temperature. To the reaction mixture, 8N-sodium hydroxide aqueous solution (13 ml), ethyl acetate (20 ml) and water (20 ml) were added. The mixture was stirred vigorously. The aqueous layer was separated from the organic layer and then extracted with ethyl acetate for 3 times. The combined organic layer was washed with water and saturated aqueous sodium chloride. The organic layer was dried over anhydrous magnesium sulfate and then evaporated. Two times of chromatography on a Silica gel column ($1^{st}$ purification: FL-60D 25 g, hexane:2-propanol=100:10/$2^{nd}$ purification: FL-60D 18 g, hexane:2-propanol=100:5) gave Compound (20) (336.4 mg, 0.918 mmol, 85.8% yield).

$^1$H-NNR Spectrum (200 MHz/CDCl$_3$) of Compound (20) δ 5.74 (1H, br), 5.45-5.36 (2H, m), 4.19-4.11 (1H, m), 3.96-3.84 (1H, m), 3.28 (2H, dq, J=5.7, 7.3 Hz), 3.05 (1H, br), 2.70-1.95 (9H, m), 2.42 (2H, t, J=7.4 Hz), 1.95-1.20 (18H, m), 1.14 (3H, t, 7.2 Hz), 0.88 (3H, t, J=7.3 Hz)

TEST EXAMPLE 1

(Method)

Whole cell patch clamp method was used to assess the effect of compound 1 (13,14-dihydro-15-keto-16,16-difluoro-PGE$_1$) and compound 2 (13,14-dihydro-15-keto-16, 16-difluoro-18 (S)-methyl-PGE$_1$) on recombinant hClC-2 chloride channel. In this example, effects of the respective compounds on Human Epithelial Kidney (HEK) cells transfected with human ClC-2 (hClC-2) were examined, and the results were compared with those on non-transfected HEK cells.

ClC-2 transfected human epithelial kidney (HEK) cells were prepared and used. HEK-293 cells obtained from American Type Culture Collection (ATCC; Manassas, Va.) were transfected with His- and T7-tagged human ClC-2 cDNA in the mammalian expression vector pcDNA3.1 (GIBCO/Invitrogen) using Lipofectamine (GIBCO/Invitrogen) for 5 h at 37° C. in serum-free medium. Cells were then resuspended in the serum-containing medium and cultured in the presence of 300 μg/ml G-418 (GIBCO/Invitrogen). The surviving cells were then expanded, tested to confirm expression of Cl- current and ClC-2 mRNA, and the cells expressing ClC-2 mRNA were frozen to store. Upon studies, the stored cells were thawed and maintained at 37° C. in 5%/95% CO$_2$/O$_2$ in MEM (GIBCO/Invitrogen) supplemented with 5% inactivated horse serum, 0.1 mM nonessential amino acids, 2 mM L-glutamine, 1 mM sodium pyruvate, 100 units/ml penicillin, and 100 μg/ml streptomycin sulfate.

In the whole cell patch clamp measurements, currents were elicited by voltage clamp pulses (1500 ms duration) between +40 mV and −140 mV, in 20 mV increments, from the beginning holding potential of −30 mV. Currents were measured 50-100 ms after start of the pulse. The external solution was normal Tyrode solution containing 135 mM NaCl, 1.8 mM CaCl$_2$, 1 mM MgCl$_2$, 5.4 mM KCl, 10 mM glucose, and 10 mM HEPES (pH 7.35). The pipette solution was 130 mM CsCl, 1 mM MgCl$_2$, 5 mM EGTA, and 10 mM HEPES (pH 7.35); also present in the pipette was 1 mM ATP—Mg$^{2+}$ (pH 7.4).

Pipettes were prepared from borosilicate glass and pulled by a two stage Narashige puller to give 1-1.5 MΩ resistance. Data were acquired with Axopatch CV-4 headstage with Digidata 1200 digitizer and Axopatch 1D amplifier. Data were analyzed using pClamp 6.04 (Axon Instruments, Foster City, Calif.), Lotus 123 (IBM) and Origin (Microcal) software.

Compound 1 and compound 2 were used at a final concentration of 1 μM in 1% DMSO.

(Result)

As shown in Table 1, there was no affection of 1% DMSO on the control currents. Cl currents in HEK cells transfected with hClC-2 (Control) were activated by 1 μM compound 1 and 1 μM compound 2. Compound 1 and compound 2 did not increase Cl currents in non-transfected cells.

These studies demonstrate that compound 1 and compound 2 are ClC-2 channel openers.

TABLE 1

Effects of compound 1 and compound 2 on Recombinant Human ClC-2 Chloride Channels

| Group | | n | Cl channel activity nS/pF | Student's t-test |
|---|---|---|---|---|
| HEK cells Transfected with hClC-2 | Control | 3 | 0.057 ± 0.008 | N.S. |
| | 1% DMSO | 3 | 0.056 ± 0.010 | |
| | Control | 3 | 0.196 ± 0.075 | p < 0.01 |
| | 1 µM compound 1 | 3 | 1.820 ± 0.114 | |
| | Control | 3 | 0.067 ± 0.026 | p < 0.05 |
| | 1 µM compound 2 | 3 | 0.558 ± 0.100 | |
| Non-transfected HEK cells | Control | 4 | 0.016 ± 0.003 | N.S. |
| | 1 µM compound 1 | 4 | 0.035 ± 0.014 | |
| | Control | 5 | 0.018 ± 0.004 | N.S. |
| | 1 µM compound 2 | 5 | 0.036 ± 0.010 | |

N.S.: Not significant.
Compound 1: 13,14-dihydro-15-keto-16,16-difluoro-PGE$_1$((−)-7-[(2R,4aR,5R,7aR)-2-(1,1-difluoropentyl)-2-hydroxy-6-oxoperhydrocyclopenta[b]pyran-5-yl]heptanoic acid)
Compound 2: 13,14-dihydro-15-keto-16,16-difluoro-18(S)-Methyl-PGE$_1$ ((−)-7-{(4aR,5R,7aR)-2-[(3S)-1,1-difluoro-3-ethylpentyl]-2-hydroxy-6-oxoperhydrocyclopenta[b]pyran-5-yl}heptanic acid)

TEST EXAMPLE 2

(Method)

16HBE14o- cells, a Human airway cell line derived from a healthy individual, which contain ClC-2 and the Cystic Fibrosis Transmembrane Regulator, Cl channel (CFTR); and CFBE41o- cells, a Human airway cell line derived from cystic fibrosis patients, which contain functional form of ClC-2 and defective form of CFTR (ΔF508 CFTR) were used. Both cells were cultured in MEM supplemented with 10% FBS (Hyclone), 20 mM 1-glutamine and penicillin/streptomycin in flasks coated with fibronectin/collagen/BSA. When desired, the cells were plated on 0.3 cm$^2$ collagen-coated permeable filters (Biocoat). After 24 hrs, the apical medium was removed so that the cells were grown in air-water interface. While they were grown in air-water interface, the basolateral side of the cells was fed with the medium and the medium was changed every other day. The cells were allowed to grow to confluence.

Short-circuit current measurements were used to evaluate Cl transport in polarized, confluent cultures of the cells grown in air-water interface. A plexiglass chamber for short-circuit current measurements in confluent cell monolayers grown on the 0.3 cm$^2$ permeable support filters was used (World Precision Instruments, Sarasota, Fla.). Electrical measurements were made with a 7402C voltage clamp device (Bioengineering Department, Iowa University). The temperature was held constant at 37° C. by circulating heated water through the water jacket of the chamber. The output of the amplifier was plotted on an analog chart recorder. Changes in short-circuit current (ΔIsc) after addition of test compounds were normalized to filter area (0.3 cm$^2$) and reported as ΔIsc/cm$^2$.

Short-circuit current measurements in the 16HBE14o- and CFBE41o- cells were carried out as described by Lofling et al. (Am J Physiol, 277(4 Pt 1):L700-8, 1999, the cited reference is herein incorporated by reference. The basolateral membrane solution contained 116 mM NaCl, 24 mM HCO$_3$, 3 mM KCl, 2 mM MgCl$_2$, 0.5 mM CaCl$_2$, 3.6 mM sodium HEPES, 4.4 mM hydrogen HEPES (pH 7.4) and 10 mM glucose; the apical membrane bath solution was identical to the basolateral membrane solution, with the exceptions that the Cl$^-$ concentration was reduced by substitution of NaCl with Na gluconate and CaCl$_2$ was increased from 0.5 mM to 2 mM to account for chelation of Ca$^{2+}$ by the gluconate. Both solutions were bubbled with CO$_2$/O$_2$ (5%/95%), which also served to help mix the solutions. In all cases, the basolateral membrane was permeabilized with 200 µg/ml nystatin.

Compound 1 and compound 2 were used at a final concentration of 1 µM. The final concentration of DMSO was 1%.

(Result)

As shown in Table 2, 1 µM compound 1 increased short-circuit current in the 16HBE14o- cells. The extent of activation by compound 1 was 9.56±0.095 µA/cm$^2$. Compound 2 also increased short-circuit current by 11.6±1.3 µA/cm$^2$ in 16HEB14o- cells. There was a large negative effect of 1% DMSO of approximately −10.5±2.0 µA/cm$^2$. Despite this large decrease in short-circuit current by DMSO, the net effect of compound 1 and compound 2 were positive in these cells.

As shown in Table 2, 1 µM compound 1 increased short-circuit current in CFBE41o- cells by 5.0±0.04 µA/cm$^2$. 1% DMSO decreased short-circuit current by −5.7±1.8 µA/cm$^2$. Despite the large negative effect of DMSO, compound 1 caused a net positive increase in Cl currents in CFBE cells.

The results show that compound 1 and compound 2 are both openers of Cl channels in 16HBE14o- cells and compound 1 is an opener of hClC-2 in CFBE41o- cells.

TABLE 2

Changes in Short-Circuit Current Using 16HBE14o- and CFBE41o- Cells

| Group | | N | Short-Circuit Current µA/cm$^2$ |
|---|---|---|---|
| 16HBE14o- cells | 1% DMSO | 3 | −10.5 ± 2.0 |
| | 1 µM compound 1 | 6 | 9.56 ± 0.95 |
| | 1 µM compound 2 | 4 | 11.6 ± 1.3 |
| CFBE41o- cells | 1% DMSO | 3 | −5.7 ± 1.8 |
| | 1 µM compound 1 | 3 | 5.0 ± 0.4 |

TEST EXAMPLE 3

(Method)

AS-HBE is a human bronchial epithelial (HBE) cell line expressing the first 131 nucleotides of CFTR in the antisense direction (antisense CFTR 16HBE14o- cells, HBE-AS; also called AS-HBE). As a result, AS-HBE cells lack CFTR transcripts and lack functional CFTR. However, AS-HBE cells do express functional ClC-2 in a manner identical to the parental cell line, 16HBE14o- cells, from which they were derived. AS-HBE cells were maintained at 37° C. in 5%/95% CO$_2$/O$_2$ in Minimal Essential Medium (MEM; GIBCO/Invitrogen, Carlsbad, Calif.) supplemented with Earl's salt, L-glutamine (GIBCO/Invitrogen), 10% heat-inactivated fetal bovine serum, 100 units/ml penicillin, 100 µg/ml streptomycin sulfate and 400 µg/ml G-418 (GIBCO/Invitrogen). The cells were grown in air-liquid interface on Biocoat inserts (Fisher Scientific, Chicago, Ill.), coated with human plasma fibronectin (GIBCO/Invitrogen) and vitrogen (Cohesion Technologies, Palo Alto, Calif.).

According to the same manner as described in Example 2, Short-circuit current measurements in the AS-HBE cells were carried out. Changes in short-circuit current (ΔIsc) were normalized to the filter area (0.3 cm$^2$) and reported as ΔIsc/cm$^2$.

Test compounds were used at a final concentration of 250 nM.

(Results)

Table 3 shows effects of test compounds on short-circuit currents in AS-HBE cells. The results show that compounds of this invention are effective ClC-2 channel openers.

TABLE 3

Effects of test compounds on short-circuit currents in AS-HBE Cells

| Group | Conc. NM | Changes in short-circuit currents (ΔIsc) μA/cm$^2$ |
| --- | --- | --- |
| Compound 1 | 250 | 4.3 |
| Compound 2 | 250 | 9.0 |
| Compound 3 | 250 | 2.7 |
| Compound 4 | 250 | 1.0 |
| Compound 5 | 250 | 0.3 |
| Compound 6 | 250 | 0.7 |
| Compound 7 | 250 | 1.0 |

Compound 1 and 2: See Test Example 1.
Compound 3: 13,14-dihydro-15-keto-16,16-difluoro-PGE$_1$N-ethyl amide (N1-ethyl-7-[(2,4aR,5R,7aR)-2-(1,1-difluoropentyl)-2-hydroxy-6-oxoperhydrocyclopenta[b]pyran-5-yl]heptanamide)
Compound 4: 15-keto-16,16-difluoro-PGE$_1$
Compound 5: 2-decarboxy-2-(2-carboxyethyl)-13,14-dihydro-15-keto-16,16-difluoro-20-ethyl-PGE$_1$isopropyl ester(Isopropyl (−)-9-[(4aR,5R,7aR)-2-(1,1-difluoroheptyl)-2-hydroxy-6-oxoperhydrocyclopenta[b]pyran-5-yl]nonanoate)
Compound 6: PGF$_{2\alpha}$
Compound 7: PGI$_2$-Na

TEST EXAMPLE 4

(Method)

According to the same manner as described in Example 1, whole cell patch clamp measurements were carried out.

Test compound induced current increases were reported as changes in pA/pF (ΔpA/pF) after addition of test compounds from the control.

Test compounds were used at a final concentration of 100 nM.

(Results)

Table 4 shows effects of test compounds on ClC-2 activation in ClC-2 transfected HEK cells. The results show that compounds of this invention are effective ClC-2 channel openers.

TABLE 4

Effects of test compounds on recombinant human ClC-2 Chloride Channels.

| Group | Concentration NM | Activation of ClC-2 channels ΔpA/pF |
| --- | --- | --- |
| Compound 1 | 100 | 39.8 |
| Compound 2 | 100 | 22.6 |

TABLE 4-continued

Effects of test compounds on recombinant human ClC-2 Chloride Channels.

| Group | Concentration NM | Activation of ClC-2 channels ΔpA/pF |
| --- | --- | --- |
| Compound 8 | 100 | 24.6 |
| Compound 9 | 100 | 38.2 |

Compound 1 and 2: See Test Example 1.
Compound 8: 13,14-dihydro-16,16-difluoro-PGE$_1$
Compound 9: 13,14-dihydro-15-keto-16,16-difluoro-PGF$_{1\alpha}$ N-ethyl amide (N1-ethyl-7-[(2,4aR,5R,6S,7aR)-2-(1,1-difluoropentyl)-2,6-dihydroxyperhydrocyclopenta[b]pyran-5-yl]heptanamide)

TEST EXAMPLE 5

(Method)

T$_{84}$ cells, a human intestinal cell line, derived form confluent monolayers with tight junctions were used. Said cell line has been widely used in studies of Cl$^-$ transport using short-circuit current (Isc). These cells contain both CFTR and ClC-2.

T$_{84}$ human intestinal epithelial cells were grown to confluence at pH 7.4 in 162-cm$^2$ flasks (Corning Costar, Mass.) with a 1:1 mixture of Dulbecco's modified Eagle's medium and Ham's F-12 nutrient mixture supplemented with 6% fetal bovine serum (FBS), 15 mM HEPES, 14.3 mM NaHCO$^3$, and antibiotics/antimycotic. Flasks were passaged weekly and fed every 3 days. Cell monolayers for experiments were grown to confluence on collagen-coated permeable support (Biocoat). Monolayers were fed every 3 days and used after stable transepithelia resistance was achieved, c.a. 7-14 days post-plating.

According to the same manner as described in Example 2, Short-circuit current measurements in T$_{84}$ cells were carried out. Changes in short-circuit current (ΔIsc) were normalized to filter area (0.3 cm$^2$) and reported as ΔIsc/cm$^2$.

Compound 1 was used at a final concentration of 50 nM.

(Results)

Table 5 shows effects of compound 1 on short-circuit currents in T$_{84}$ cells. The result shows that compound 1 activated Cl$^-$ transport in a human intestinal cell line, T$_{84}$.

TABLE 5

Effect of compound 1 on short-circuit currents in T$_{84}$ cells

| Group | Concentration nM | Changes in short-circuit currents (ΔIsc) μA/cm$^2$ |
| --- | --- | --- |
| Compound 1 | 50 | 56.5 |

Compound 1: See Test Example 1.

TEST EXAMPLE 6

(Method)

Compound 1 (13,14-dihydro-15-keto-16,16-difluoroprostaglandin E$_1$) of 1, 10 or 100 μg/kg in the volume of 5 mL/kg was orally administered to male Wistar rats (six weeks old, weight:180-210 g) that had been fasted for at least 16 hours. The control group received the same volume of vehicle (distilled water containing 0.5% ethanol and 0.01% polysorbate 80). Thirty minutes after the administration, the animals were subjected to laparotomy under ether anesthesia. The top portion of the duodenum and the end portion of the ileum were ligated respectively, and the bowel was extirpated. The intestinal fluid of each animal was collected and centrifuged by 10,000×g for 5 minutes. Supernatant was collected, and the concentration of chloride ion in the supernatant of intestinal fluid was measured with a chloride counter (CL-7, Hiranuma Sangyo Co., Ltd.). Dunnett's test was used in the comparison of the control group and the groups receiving Compound 1 in each dose. P values less than 0.05 were considered to be statistically significant.

(Result)

Table 6 shows the concentration of chloride ion in the intestinal fluid of each group. Administration of Compound 1 of 1, 10 and 100 μg/kg increased the concentration of chloride ions in the bowel in a dose-dependant manner. Compared with the control group, the group receiving Compound 1 of 1 μg/kg showed significant increase in the concentration of chloride ions in the intestinal fluid.

The above result indicates that Compound 1 opens chloride channels in the bowel to promote positively the chloride ion transport.

TABLE 6

Effect of Compound 1 on the Chloride Ion Transport into Intestinal Fluid of Rats

| Group | | n | Chloride Ion Concentration in Intestinal Fluid Mean ± S.E., mEq/L |
|---|---|---|---|
| Control | (Vehicle) | 7 | 41.8 ± 3.9 |
| Compound 1 | 1 μg/kg P.O. | 7 | 82.2 ± 7.0** |
| Compound 1 | 10 μg/kg P.O. | 7 | 110.1 ± 5.6** |
| Compound 1 | 100 μg/kg P.O. | 7 | 126.6 ± 2.4** |

Dunnett's Test: Compared with the Control Group,
**$P < 0.01$

TEST EXAMPLE 7

(Method)

Compound 2 (13,14-dihydro-15-keto-16,16- difluoro-18 (S)-methyl-prostaglandin $E_1$) of 100 μg/kg was orally administered to male Wistar rats (six weeks old, weight: 180-210 g) three times a day for seven days. The control group (n=7) received the same volume of vehicle (distilled water containing 0.01% polysorbate 80 and 0.5% ethanol). In the following morning of the final administration day (about 17 hours after the final administration), a polyethylene catheter (PE10, Becton Dickinson and Company) was inserted in the rats' choledoch under ether anesthesia. The rats were placed into Borrmann's cages and were left for 1 hour to awake from anesthesia. Bile discharged in one hour, from one to two hours after the insertion of the catheter, was collected and the concentration of chloride ion in the bile was measured with a chloride counter (CL-7, Hiranuma Sangyo Co., Ltd.). Student's t-test was used in the comparison of the control group and the group receiving Compound 2. P values less than 0.05 were considered to be statistically significant.

(Result)

Table 7 shows the concentration of chloride ions in the bile of each group. Compared with the control group, the concentration of chloride ions in the bile of the group receiving Compound 2 increased significantly.

The above result indicates that Compound 2 opens chloride channels in the liver to promote positively the chloride ion transport.

TABLE 7

Effect of Compound 2 on the Chloride Ion Transport into Bile in Rats

| Group | Dose μg/kg, t.i.d. for 7 days, P.O. | n | Chloride Ion Concentration in Bile Mean ± S.E., mEq/L |
|---|---|---|---|
| Contr. (Vehicle) | — | 7 | 91.1 ± 2.7 |
| Compound 2 | 100 μg/kg P.O. | 8 | 98.4 ± 1.8* |

Student's t-test: Compared with the Control Group,
*$P < 0.05$

TEST EXAMPLE 8

(Method)

Physiological saline, eye drops vehicle, or eye drops containing 0.0001% or 0.001% of Compound 1 was instilled to male white rabbits in the volume of 30 μL/eye. Before the instillation (0 hour) and at 2, 4, 6 and 8 hours after the instillation, lacrimal fluid 5 μL was collected from the conjunctival sac of palpebra inferior with a capillary pipette. The collected lacrimal fluid was diluted five fold with distilled water, and the concentration of chloride ions was measured with a chloride counter (CL-7, Hiranuma Sangyo Co. Ltd.). Student's t-test and Wilcoxon's test were used in the comparison of the control group and the groups receiving Compound 1 in each dose. P values less than 0.05 were considered to be statistically significant.

(Result)

Table 8 shows the concentration of chloride ions in the lacrimal fluid of each group. Compared with the control group, Compound 1 increased the concentration of chloride ions in the lacrimal fluid in a dose-dependant manner. Compared with the control group, the group receiving 0.0001% eye drops of Compound 1 and the group receiving 0.001% eye drops of Compound 1 showed significant increase in the concentration of chloride ions in the lacrimal fluid at 4 and 8 hours after the instillation and 2, 4 and 8 hours after the instillation, respectively.

The above result indicates that test Compound 1 opens chloride channels in the eye by instillation to promote positively the chloride ion transport.

TABLE 8

Effect of Compound 1 on the Chloride Ion Transport into Lacrimal Fluid in Rabbits

| Group | n | Chloride Ion Concentration, Mean ± S.E., mEq/L Time after Instillation (hr.) | | | | |
|---|---|---|---|---|---|---|
| | | Pre | 2 | 4 | 6 | 8 |
| Saline | 8 | 133.3 ± 4.5 | 132.6 ± 2.7[##] | 132.2 ± 2.0 | 132.4 ± 2.0 | 130.6 ± 1.8 |
| Vehicle | 8 | 136.6 ± 3.2 | 116.9 ± 1.3 | 128.1 ± 3.1 | 132.4 ± 2.2 | 132.8 ± 1.6 |
| 0.0001% Compound 1 | 8 | 136.7 ± 3.6 | 123.4 ± 5.2 | 136.8 ± 2.3[#] | 136.8 ± 2.0 | 140.8 ± 2.8[#] |
| 0.001% Compound 1 | 8 | 135.4 ± 4.0 | 152.9 ± 7.7[##] | 151.4 ± 2.9[##] | 138.9 ± 3.3 | 138.8 ± 1.6[#] |

Student's t-test: Compared with the Control Group, [#]$P < 0.05$, [##]$P < 0.01$
Wilcoxon's test: Compared with the Control Group, [#]$P < 0.05$, [##]$P < 0.01$

What is claimed is:

1. A compound represented by formula (IV):

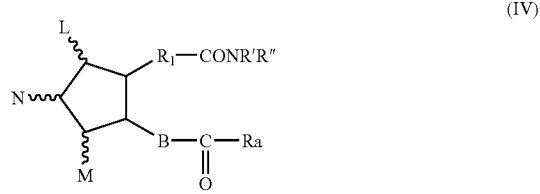

(IV)

wherein L, M and N are hydrogen, hydroxy, halogen, lower alkyl, hydroxy(lower)alkyl, or oxo, wherein at least one of L and M is a group other than hydrogen, and the five-membered ring may have one or more double bonds;

R' and R" are hydrogen, lower alkyl, aryl, alkyl- or aryl-sulfonyl, lower alkenyl or lower alkynyl;

B is —CH$_2$—CH$_2$—, —CH=CH— or —C≡C—;

$R_1$ is a saturated or unsaturated bivalent lower or medium aliphatic hydrocarbon residue, which is unsubstituted or substituted with halogen, alkyl, hydroxy, oxo, or aryloxy, and at least one carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, or aryloxy; cyclo(lower)alkyl; cyclo(lower)alkyloxy; aryl; or aryloxy.

2. The compound as described in claim 1, wherein said compound is 13,14-dihydro-15-keto-16,16-difluoro-PGE$_1$ N-ethyl amide.

3. The compound as described in claim 1, wherein said compound is 13,14-dihydro-15-keto-16,16-difluoro-PGF$_{1\alpha}$ N-ethyl amide.

4. The compound as described in claim 1, wherein said compound is 13,14-dihydro-15-keto-17-phenyl-18,19,20-trinor-PGF$_{2\alpha}$ N-ethyl amide.

5. The compound as described in claim 1, wherein said compound is 13,14-dihydro-15-keto-20-ethyl-PGF$_{2\alpha}$ N-ethyl amide.

* * * * *